United States Patent [19]

Ramsey et al.

[11] Patent Number: 5,797,344
[45] Date of Patent: *Aug. 25, 1998

[54] ON-DEMAND USEFUL LIFE INDICATOR AND METHOD OF MAKING SAME

[76] Inventors: Joseph W. Ramsey, 11 Great Meadow La., East Hanover, N.J. 07936; Peter L. Gill, 1 Kenley Way, Hackettstown, N.J. 07840

[*] Notice: The term of this patent shall not extend beyond the expiration date of Pat. No. 5,630,372.

[21] Appl. No.: 816,970

[22] Filed: Mar. 13, 1997

[51] Int. Cl.⁶ .................................................. G01D 21/00
[52] U.S. Cl. .................................................. 116/206
[58] Field of Search ......................... 116/206, 207, 116/216, 217; 426/87, 88; 436/902, 904, 905; 374/102, 106, 161, 162

[56] References Cited

U.S. PATENT DOCUMENTS

| | | | |
|---|---|---|---|
| 3,018,611 | 1/1962 | Biritz | 116/206 X |
| 3,420,635 | 1/1969 | Davis | 116/206 X |
| 3,480,402 | 11/1969 | Jackson | 116/206 X |
| 4,205,043 | 5/1980 | Esch et al. | 116/206 X |
| 4,812,053 | 3/1989 | Bhattacharjee | 374/102 |
| 5,630,372 | 5/1997 | Ramsey et al. | 116/206 |

FOREIGN PATENT DOCUMENTS

| 93983 | 5/1985 | Japan | 116/206 |
|---|---|---|---|

*Primary Examiner*—Diego F. F. Gutierrez
*Assistant Examiner*—Willie Morris Worth
*Attorney, Agent, or Firm*—Patrick J. Pinto

[57] ABSTRACT

An on demand useful life indicator (10) and method providing a uniform visual change. The indicator (10) attachable to goods or worn. This indicator includes a base (12); indicator material (14), impermeable adhesive (16), and a co-layered covering (18). The indicator material (14) provides a visual indication when exposed to a selected component of an ambient fluid. The indicator material (14) is intimately fixed to one side of a second layer (22) of the covering (18) in a selected pattern. The adhesive layer (16) is applied in a selected pattern between the base member (12) and the covering material (18). A permeable second layer (22) of the covering (18) is adhered to the adhesive layer (16) allowing an impermeable first layer (20) to be selectively removed therefrom. The useful life indicator remains in a selected state of dormancy until removal of the first layer (2).

18 Claims, 1 Drawing Sheet

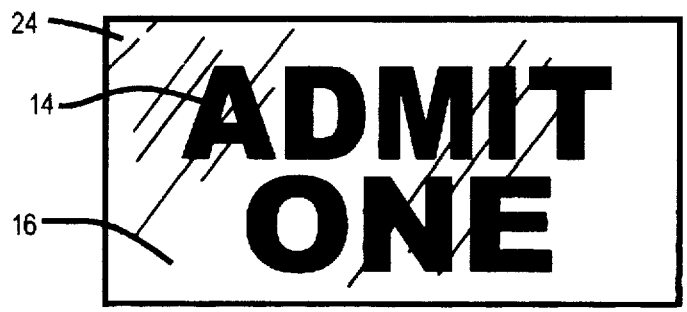
FIG. 1
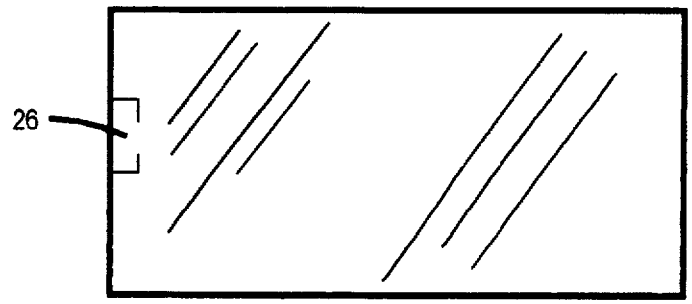
FIG. 2
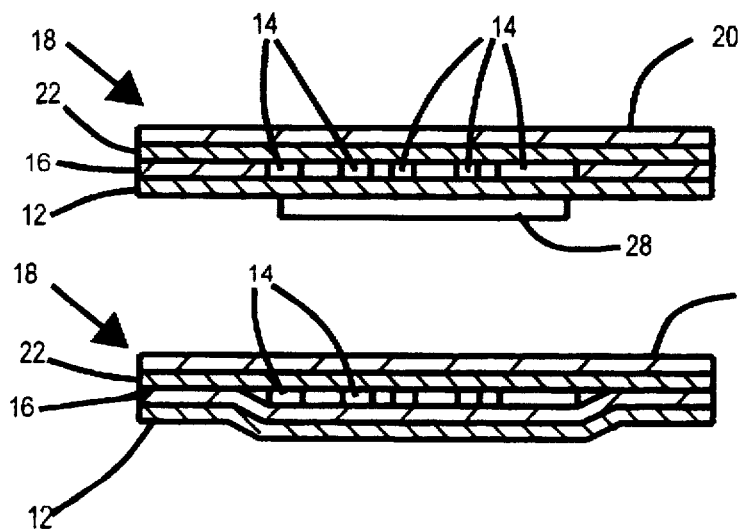
FIG. 3
FIG. 4

ON-DEMAND USEFUL LIFE INDICATOR AND METHOD OF MAKING SAME

BACKGROUND OF THE INVENTION

1. Field of the Invention

With regard to the classification of art, this invention is believed to be found in the general class entitled SIGNALS AND INDICATORS and more particularly to those subclasses pertaining to those that are CHEMICALLY ACTIVATED.

2. Description of Related Art

Useful life indicators are known in the prior art. Some examples of the known prior art are: U.S. Pat. No. 3,018,611, that issued to Biritz on Jan. 30, 1962; U.S. Pat. No. 3,243,303 that issued to Johnson on Mar. 29, 1966; U.S. Pat. No. 4,205,043 that issued to Esch et al on May 27, 1980; U.S. Pat. No. 4,212,153 that issued to Kydonieus on Jul. 15, 1980; U.S. Pat. No. 4,812,053 that issued to Bhattacharjee on Mar. 14, 1989; and U.S. Pat. application Ser. No. 08/506,334 that was filed by and is solely owned by the present inventors on Jul. 25, 1995, and is now allowed U.S. Pat. No. 5,630,371. All of the known prior art have advanced the art. Many of the known prior art patents enclose an indicating material between an impervious substrate and a perforate transparent cover. Many of the known prior art patents rely on color migration or wicking for providing the determination of the timing period. This known construction has some deficiencies which include variation of uniformity of the intensity of color or uniform lack of color over the total surface of the indicating material. This means that an observer who is monitoring the time indicator may not accurately assess the status because of that non-uniformity of color shade or intensity or lack thereof near the end of the timing period. The non-uniformity of color or lack of color may manifest itself as stripes, blotches and the like. This may mean that the product or the services may either be extended beyond a useable life or prematurely terminated.

It has been discovered that a uniformity of the intensity of color is dependent on the uniformity of the thickness, density, and homogenous blending of the indicating material and the uniformity of exposure to a selected component of an ambient fluid. Some of the known prior art patents suggest using a strip of paper that is impregnated with an indicating solution. Any variation in absorbency of the strip of paper will also result in a lack of uniformity in a change in color over its entire surface. It has also been discovered that any voids between the indicator material and any cover material will contribute to the perceived lack of uniformity of color change. Another condition that has been identified as resulting in a non-uniform display is when an indicating material is applied as a coating over an adhesive covered base member or substrate having a surface containing peaks and valleys. The use of a self-leveling indicating material over those peaks and valleys will inherently result in variations in thickness of the indicator material. The use of an indicator material that follows the contour of the base member will inherently produce a corrugated-like surface resulting in voids between the surface of the indicating material and a cover material. Any voids therein may also result in condensation being formed in those voids under certain conditions. Any waviness in the surface of the covering material will also contribute to reading errors. All of the above conditions singularly or in combination will contribute to observer error in the reading of the uniformity of color of the known useful life or time indicators. Some of the known prior art are also temperature sensitive which means that the timing period is altered by changes in temperature. Some of these same patents, using heat sealing techniques in the assembly of their indicators, may have inherent timing tolerance problems. Others rely on migration of an ambient fluid through permeable adhesives. Oxidation of the adhesives during storage may further contribute to non-uniformity of color or lack of color or timing errors by clogging perforations with residue.

The present invention addresses those above identified needs and deficiencies. The present invention provides a novel structure that allows at least one of its indicating portions to remain dormant while being stored, at normal ambient temperatures and relative humidity, between the time of manufacture and the time of selected activation. The present invention also discloses a useful life indicator and method of making the same that provides a substantially uniform change of color or lack of color over the entire surface of at least one selected active area of the indicator material. The present invention also provides a useful life indicator that has its indicator material intimately applied or fixed to its permeable membrane. The construction and method, disclosed below, provides a useful life indicator that includes an indicating material having a substantially uniform thickness throughout at least one active indicator material area. It also substantially eliminates any voids between the indicating surface and the permeable membrane. After activation, as described below, the present invention provides an indication means that is activated by a component of an ambient fluid. The observable indication has a substantially uniform intensity of color over the entire selected active surface of the useful life indicator during the predetermined timing period. This uniformity of color or lack of color substantially eliminates timing period errors due to the observers perception of the shade or intensity of the end color or lack of color. The permeable membrane member also protects the indicator material during the user activated timing period that begins only after a co-layered impermeable layer has been removed.

The present invention is practical, reliable, and compact. The present invention is also economical to manufacture, apply, and use.

SUMMARY OF THE INVENTION

This invention may be briefly summarized as an on demand usable life indicator comprising: a) a co-layered cover member having at least two layers, a first layer of the two layers being impermeable to a selected ambient fluid. The first layer may be transparent, fully opaque, or partially opaque, a second layer of the two layers being permeable to the selected ambient fluid; b) an indicator material having a first side and an opposite second side, the first side being intimately fixed to one side of the second layer opposite the first layer in a predetermined pattern, the indicator material having a selected composition providing a visual indication when exposed to a predetermined active component of the ambient fluid; c) an adhesive applied with a predetermined pattern on a same side of the second layer of the cover member as the indicator material, the adhesive being impermeable with respect to the active component of the ambient fluid; d) a base member being fixed to the adhesive while fully covering the opposite side of selected portions of the predetermined pattern of the indicator material; and wherein the second layer providing a membrane between the ambient fluid and the indicator material, the first layer is selectably removable from the second layer for exposing the second layer, thus enabling the predetermined active component of the ambient fluid to permeate through the exposed second layer thereby equally and uniformly exposing a selected portion of the predetermined pattern of the indicating material to the selected ambient fluid, to provide a uniform visual indication, being observable through the exposed surface of the second layer, the visual indication beginning after removal of the first layer and being completed near the end of a predetermined period of time.

The useful life indicator of the present invention may also include a self contained reference norm for providing a comparative reading with the active indicating material.

The present invention may be mounted on an article by an adhesive strip and the like but not limited thereto. It also may be attached and worn by an individual by means of a pin, clasp or the like for monitoring valid access times to an entertainment event, exposure to hazardous substances and the like.

In addition to the above summary, the following disclosure is intended to be detailed to insure adequacy and aid in the understanding of the invention. However, this disclosure, showing particular embodiments of the invention, is not intended to describe each new inventive concept which may arise. These specific embodiments have been chosen to show at least one preferred or best mode for the on demand useful life indicator of the present invention. These specific embodiments, as shown in the accompanying drawings, may also include diagrammatic symbols for the purpose of illustration and understanding.

BRIEF DESCRIPTION OF THE DRAWING

FIG. 1 represents a plan view of an on demand useful life indicator of the present invention. This view depicting indicia that is visible either prior to or after exposure to an ambient fluid.

FIG. 2 represents a plan view of an on demand useful life indicator of the present invention. This view depicting indicia that is not visible either prior to or after exposure to an ambient fluid.

FIG. 3 represents a side elevation view, in section and in an enlarged scale, depicting a first type of construction.

FIG. 4 represents a side elevation view, in section and in an enlarged scale, depicting an alternate type of construction.

In the following description and in the appended claims, various details are identified by specific names for convenience. These names are intended to be generic in their application while differentiating between the various details. The corresponding reference numbers refer to like members throughout the several figures of the drawing.

The figures of drawing accompanying and forming a part of this specification disclose details of construction for the sole purpose of explanation. It is to be understood that structural details may be modified without departing from the concept and principles of the claimed invention. This invention may be incorporated into other structural forms than those that are shown.

DETAILED DESCRIPTION OF THE INVENTION

Referring to the drawings, FIG. 1 through FIG. 4, a usable life indicator is generally identified as 10. That usable life indicator 10 includes a base member 12, an indicator material layer 14; an adhesive layer 16; and a co-layered cover member 18. The components are similar to the components disclosed in our co-pending U.S. Pat. application Ser. No. 08/506,334 that was filed by the present inventors on Jul. 25, 1995, that is now allowed and is incorporated by reference to the extent that the present law allows.

This co-layered cover member 18 includes at least two layers. It is preferred that the major surfaces of the two layers are substantially equal but not limited thereto. This preference lends itself to the automated and economical production of the present invention. The outer or first layer 20 is impermeable to the selected component of the ambient fluid. As previously mentioned the outer layer 20 need not be transparent. Preferably, the inner or second layer 22 is uniformly permeable to the selected component of the ambient fluid. In the context of this application, the term co-layered material means a class of materials in which the faying surfaces of the first layer and second layer abut in an intimate relationship. The first layer is selectably peelable from the co-layered second layer. It is preferred that the first layer be of a plastic material such as a polyester but not limited thereto. The first layer 20 should have a smooth surface finish onto which the second layer is applied. The application of the second layer to the first layer should result in a smooth surface finish absent peaks and valleys. The application of the second layer to the first layer must not include any intermediate agents that would effect the permeability of the second layer. One example of a class of co-layer materials is commercially available from Micron Coating Inc. under the name "SORBICOTE" but not limited thereto The indicator material layer 14 is intimately fixed to an exposed surface of the second layer 22 of the co-layered covered member 18. The term intimately fixed, in the context of this disclosure, means that at least one selected area of the indicating material has been uniformly applied and fixed to the co-layered cover member so that substantially no voids are present between the abutting first side of the indicating material 14 and the second layer 22.

Printing the indicator material 14 in a selected pattern is one of the methods of application but not limited thereto. This indicator material 14 preferably has a selected composition that will provide a uniform visual indication when exposed to a selected component of an ambient fluid for a predetermined selected period of time. Some examples will be given below. This indication may be manifested either as a change from a lack of color to a visual color, as depicted as the change from FIG. 2 to FIG. 1 or a change from a visual color to a lack of color, as depicted as the change from FIG. 1 to FIG. 2. It may be necessary to apply this indicator material in a controlled or inert atmosphere such as Nitrogen. The selected component should be absent from the controlled atmosphere for avoiding a false indication. It may be necessary to heat, cure or dry the indicator layer to a preferred uniform thickness and state prior to the application of the other components of the useful life indicator 10.

The rate of change of the visual indication of the indicator material layer 14 may be controlled by its composition, thickness, and/or by controlling the permeability of the inner or second layer 22. The inner layer 22 also acts as a membrane for protecting the surface of the adhesive layer 16 and the indicator material layer 14 from abrasion during its active timing period.

After the indicator material layer 14 is brought to a preferred cured condition, the adhesive layer 16 may be applied either in a selected pattern covering selected portions of the indicator material 14 or thereover as depicted in FIG. 4. Alternatively, the adhesive layer may be applied in a selected pattern surrounding the indicator material as depicted in FIG. 3, by a process such as printing; coating; or laminating. Preferably, the adhesive layer 16 is composed of a material that is impermeable to the selected component of the ambient fluid. This adhesive layer may be pressure sensitive; heat activated; or a contact type. The inner layer 22 preferably has a greater adhesion to the adhesive layer 16 than to the outer layer 20. This allows the outer layer 20 to be selectively removed from indicator 10 without removal of the inner layer 22 from the indicator layer 14 and the adhesive layer. Removal of the outer layer 20 allows a selected component of the ambient fluid to uniformly permeate through the inner layer 22 to and towards the indicator material 14. The adhesive 16 may be eliminated in at least one place such as corner 24, in order to facilitate the manual removal of the first layer 20 at the time of selected activation. Alternatively a silicone varnish coating may be selectively applied between the second layer 22 and the adhesive 16 at a convenient position such as corner 24.

The base member 12 is applied or fixed to the exposed side of the adhesive 16 while completely covering the indicating material 14. The base member 12 is preferably made of a material that is impermeable to a selected ambient fluid but not limited thereto. A permeable base member 12 may be used when the adhesive, depicted in FIG. 4, is impermeable and a shortened storage time can be tolerated. The ambient fluid may be either a gas or a liquid. However the base member 12 may be made of a material that is impervious to gas and liquid. This base member 12 may be a flexible thermoplastic material, a metallic foil, or a semi rigid member. The base member 12 may further include an attaching means 28. Examples of the attaching means 28 are a self-adhesive label, a safety pin, clasp, hook and loop fastener or the like. It has been found that the base member 12 may be applied as a base member 12/adhesive 16 laminate. The application of the base member/adhesive laminate improves the automated handling of the various components of the useful life indicator of the present invention.

The usable life indicator 10 has a relatively long shelf life when the outer layer and the impermeable base member 12 are not punctured. It is only after removal of the outer layer 20 that the timing of the active period for a selected useful life begins.

The edges of the indicating material 14 are preferably isolated from exposure to the selected component of the ambient fluid by a perimeter frame of impermeable adhesive 16, as depicted in FIG. 3 and FIG. 4. This perimeter frame need only be of a minimal width such as in the neighborhood of 1.6 mm (0.062 in.).

The composition of the adhesive layer 16 may be formulated to include the selected component of the ambient fluid. This type of formulation would provide a perceptible change to any indicator material 14 directly in contact with the adhesive layer 16. In this alternate embodiment, the adhesive 16 would only be in intimate contact with selected and isolated portions or elements of the indicating material 14. This arrangement would provide a self-contained norm for judging the degree of color or lack of color. This arrangement would compensate for variations in color between various batches or formulations of indicating material 14. Alternatively a reference indicating material 26 may be positioned along the edge of the useful life indicator, as depicted in FIG. 3. This reference point 26 may also be used as an indicator for a second timing period that may indicate elapsed storage time or elapsed time from a date of manufacture, for warranty purposes.

One example of a useable life indicator includes an indicator material layer 14 that is sensitive to an acid or a base component of the ambient fluid. The indicator material 14 may be formulated with litmus like properties uniformly blended therein. Some examples of materials having litmus properties are Phenolphthalein, Phenolsulfonethalein and the like.

A second example of a useable life indicator includes an indicator material layer 14 that is sensitive to carbon dioxide as the active component of the ambient fluid. The indicator material 14 may be formulated with Oxidation/Reduction properties uniformly blended therein. One example of those materials that change properties when exposed to carbon dioxide is Thymolphthalein, but not limited thereto.

A third example of a useable life indicator includes an indicator material layer 14 that is sensitive to oxygen as the active component of the ambient fluid. The indicator material 14 may be formulated with Oxidation/Reduction properties uniformly blended therein. One example of those materials that change properties when exposed to oxygen is Methyl Orange, but not limited thereto.

A fourth example of a useable life indicator includes an indicator material layer 14 that is sensitive to ozone as the active component of the ambient fluid. The indicator material 14 may be formulated with Oxidation/Reduction properties uniformly blended therein. One example of those materials that change properties when exposed to ozone is Crystal Violet, but not limited thereto.

A fifth example of a useable life indicator includes an indicator material layer 14 that is sensitive to chlorine as the active component of the ambient fluid. The indicator material 14 may be formulated with Oxidation/ Reduction properties uniformly blended therein. One example of those materials that change properties when exposed to chlorine is Metacresol Purple, but not limited thereto.

A sixth example of a useable life indicator includes an indicator material layer 14 that is sensitive to carbon monoxide as the active component of the ambient fluid. The indicator material 14 may be formulated with Oxidation/ Reduction properties uniformly blended therein. One example of those materials that change properties when exposed to carbon monoxide is Alizarin Yellow, but not limited thereto.

As mentioned above, the adhesive layer 16 in any or all of the examples mentioned above may be formulated with the component of the ambient fluid blended therein to provide the norm as also described above. The color or visual indication of that selected area of the indicator material 14 isolated from and not in contact with the adhesive would remain as applied until the outer layer 20 is removed. The area of the indicator material 14 in direct contact with the adhesive layer 16 would change to the color or visual indication that is to be used as a comparative norm or reference.

As previously noted, the first layer 20 may include as least one opaque portion. This opaque portion will provide a visual indication to an observer that the first layer remains in place. The opaque portion may include instructions, indicia and the like.

It is preferred that the composition of the indicating material 14 provide an overall accuracy of timing periods that have a predetermined tolerance not greater than fifteen percent. By composition, it is meant to include thickness, density, homogeneous blending and the like. It has been found that a tolerance in the neighborhood of ten percent when exposed to relative humidity between 5 percent and 95 percent and/or a temperature range between −25 C. and 50 C. meets most applications.

It is anticipated that the Indicating material may be applied in several distinct areas. One non-limiting example is a first area having a selected first thickness that is different from a second area having a second thickness. The first and second areas will develop to the same uniform color or lack of color but only in different timing periods.

The present invention provides a useful life indicator 10 and construction that produces uniform color change in at least one selected area while providing crisp indicia and graphics that are easy to read and assess.

The present invention may be produced as individual discrete time indicators 10 as described above. The compactness and thin profile of the construction of the present invention also provide for the alternative delivery of individual or discrete indicators on a carrier strip for automatic application by conventional labeling or dispensing machinery. The indicators 10 may be individually die cut so that the first layer 20 remains as the continuous carrier strip. The indicators may be provided in magazines, reels and the like for use by and with those labeling or dispensing machines. The carrier strip or first layer 20 would be automatically removed as each indicator is applied to the article to be monitored. As a second alternate, the 10 may individually die cut leaving a continuous carrier strip in the form of a peelable backing strip of the adhesive attachment means 28. It this second alternate, the discrete indicators are also supplied in a form for application by labeling or dispensing machines. In the second alternate, the first layer 20 may be selectively and manually removed at a later time to begin the timing period.

The foregoing discussion also suggests a method for making a useful life indicator comprising the steps of:

a) providing a co-layered cover member having at least two layers, a first layer of the two layers being impermeable to a selected ambient fluid, a second layer of the two layers being permeable to the selected ambient fluid;

b) intimately fixing an indicator material having a first side and an opposite second side to one side of the second layer opposite the first layer in a predetermined pattern, the indicator material having a selected composition providing a visual indication when exposed to a predetermined active component of the ambient fluid;

c) applying an adhesive in a predetermined pattern on a same side of the second layer of the cover member as the indicator material, the adhesive being impermeable with respect to the active component of the ambient fluid;

d) providing a base member in a fixed relationship to the adhesive while fully covering the opposite side of selected portions of the predetermined pattern of the indicator material; and wherein the second layer providing a membrane between the ambient fluid and the indicator material, the first layer is selectably removable from the second layer for exposing the second layer, thus enabling the predetermined active component of the ambient fluid to permeate through the exposed second layer thereby equally and uniformly exposing a selected portion of the predetermined pattern of the indicating material to the selected ambient fluid, to provide a uniform visual indication being observable through the exposed surface of the second layer, the visual indication beginning after removal of the first layer and being completed near the end of a predetermined period of time.

Directional terms such as "upper", "lower", "inner", "outer" and the like may have been used in the description. These terms are applicable to the embodiments shown and described in conjunction with the drawings. These terms are merely used for the purpose of description in connection with the drawings and do not necessarily apply to the position in which the present invention may be used.

While these particular embodiments of the present invention have been shown and described, it is to be understood that the invention is not limited thereto and protection is sought to the broadest extent that the prior art allows.

What is claimed is:

1. An improved useful life indicator including:

a) a co-layered cover member having at least two layers, a first layer of the two layers being impermeable to a selected ambient fluid, a second layer of the two layers being permeable to the selected ambient fluid;

b) an indicator material having a first side and an opposite second side, said first side being intimately fixed to one side of the second layer opposite the first layer in a predetermined pattern so that any abutting surfaces of said one side and said first side being absent any voids therebetween, said indicator material having a selected composition providing a visual indication when exposed to a predetermined active component of the ambient fluid;

c) an adhesive applied with a predetermined pattern on a same side of the second layer of the cover member as the indicator material, said adhesive being impermeable with respect to the active component of said ambient fluid;

d) a base member being fixed to the adhesive while fully covering the opposite side of selected portions of the predetermined pattern of the indicator material; and wherein the second layer provides a membrane between the ambient fluid and the indicator material, the first layer is selectably removable from said second layer for exposing said second layer, thus enabling the predetermined active component of the ambient fluid to permeate through the exposed second layer thereby equally and uniformly exposing a selected portion of the predetermined pattern of the indicating material to the selected ambient fluid, to provide a visual indication being observable through the exposed surface of the second layer, the visual indication beginning after removal of said first layer and being completed near the end of a predetermined period of time.

2. An improved useful life indicator as recited in claim 1 wherein the base member is impermeable to the selected component of an ambient fluid.

3. An improved useful life indicator as recited in claim 1 wherein the exposed membrane providing abrasion protection for at least one portion of the indicating material thereunder.

4. An improved useful life indicator as recited in claim 1 wherein the selected composition of the indicator material includes litmus properties, and the adhesive layer further including a predetermined pH factor for bringing the indicator material in contact with said adhesive layer to a reference state of indication for providing a visual comparison with the visual indication provided by said at least one selected portion of the indicator material.

5. An improved useful life indicator as recited in claim 1 wherein the base member includes an attaching means that is positioned on the base member on its surface opposite to the adhesive.

6. An improved useful life indicator as recited in claim 1 wherein the base member is a flexible thermoplastic material.

7. An improved useful life indicator as recited in claim 1 wherein the predetermined active component of the ambient fluid is carbon monoxide.

8. An improved useful life indicator as recited in claim 1 wherein the predetermined active component of the ambient fluid is oxygen.

9. An indicator as recited in claim 1 wherein the predetermined active component of the ambient fluid is chlorine.

10. An improved useful life indicator as recited in claim 1 wherein the predetermined active component of the ambient fluid is ozone.

11. An improved useful life indicator as recited in claim 1 wherein a thickness of the indicator material between the first side and the second side is uniform.

12. An improved useful life indicator as recited in claim 1 wherein the first layer is also an elongated continuous carrier strip carrying a plurality of discrete useful life indicators.

13. An improved useful life indicator as recited in claim 5 wherein the attaching means is an adhesive strip having a peelable backing strip; and said backing strip is an elongated continuous carrier strip for a plurality of discrete useful life indicators.

14. A method for making an improved useful life indicator including the steps of:
   a) providing a co-layered cover member having at least two layers, a first layer of the two layers being impermeable to a selected ambient fluid, a second layer of the two layers being permeable to the selected ambient fluid;
   b) intimately fixing an indicator material having a first side and an opposite second side to one side of the second layer opposite the first layer in a predetermined pattern so that any abutting surfaces of said one side and said first side being absent any voids therebetween, said indicator material having a selected composition providing a visual indication when exposed to a predetermined active component of the ambient fluid;
   c) applying an adhesive in a predetermined pattern on a same side of the second layer of the cover member as the indicator material, said adhesive being impermeable with respect to the active component of said ambient fluid;
   d) fixing a base member to the adhesive while fully covering the opposite side of selected portions of the predetermined pattern of the indicator material; and wherein the second layer provides a membrane between the ambient fluid and the indicator material, the first layer is selectably removable from said second layer for exposing said second layer, thus enabling the predetermined active component of the ambient fluid to permeate through the exposed second layer thereby equally and uniformly exposing a selected portion of the predetermined pattern of the indicating material to the selected ambient fluid, to provide a visual indication being observable through the exposed surface of the second layer, the visual indication beginning after removal of said first layer and being completed near the end of a predetermined period of time.

15. A method for making an improved useful life indicator as recited in claim 14 including the further step of positioning an attaching means on the base member on its surface opposite to the adhesive.

16. A method for making an improved useful life indicator as recited in claim 14 including the further step of providing a second area of indicator material acting as a self contained norm providing a visual comparison with the visual indication provided by said at least one selected portion of the indicator material.

17. An improved useful life indicator as recited in claim 15 wherein the attaching means is an adhesive strip having a peelable backing strip; and said backing strip is also an elongated continuous carrier strip for a plurality of discrete useful life indicators.

18. An improved useful life indicator as recited in 14 wherein the first layer is also an elongated continuous carrier strip carrying a plurality of discrete useful life indicators.

* * * * *